(12) United States Patent
Bellier et al.

(10) Patent No.: US 9,429,555 B2
(45) Date of Patent: Aug. 30, 2016

(54) DEVICE FOR MEASUREMENT COUPLED WITH WATER PARAMETERS OF SOIL

(75) Inventors: Gerard Bellier, Le Plessis Trevise (FR); Erik Braudeau, Rosny Sous Bois (FR)

(73) Assignees: VALORHIZ, Montferrier sur Lez (FR); IRD, Marseille (FR)

( * ) Notice: Subject to any disclaimer, the term of this patent is extended or adjusted under 35 U.S.C. 154(b) by 418 days.

(21) Appl. No.: 14/130,370

(22) PCT Filed: Mar. 7, 2012

(86) PCT No.: PCT/FR2012/050469
§ 371 (c)(1),
(2), (4) Date: Jan. 17, 2014

(87) PCT Pub. No.: WO2013/004927
PCT Pub. Date: Jan. 10, 2013

(65) Prior Publication Data
US 2014/0123738 A1    May 8, 2014

(30) Foreign Application Priority Data

Jul. 5, 2011 (FR) ...................................... 11 56036

(51) Int. Cl.
*G01N 33/24* (2006.01)
*G01N 35/04* (2006.01)

(52) U.S. Cl.
CPC ..... *G01N 33/246* (2013.01); *G01N 2035/0441* (2013.01)

(58) Field of Classification Search
CPC .................. G01N 333/246; G01N 2035/0441; B01L 2200/025; B01L 9/06; B01L 2300/0829
See application file for complete search history.

(56) References Cited

U.S. PATENT DOCUMENTS

| | | | | |
|---|---|---|---|---|
| 3,872,717 A | * | 3/1975 | Fox | G01N 3/42 73/84 |
| 5,147,551 A | * | 9/1992 | Averette | B01D 11/0219 210/472 |
| 5,320,808 A | * | 6/1994 | Holen | B01L 3/508 141/130 |
| 5,507,410 A | * | 4/1996 | Clark | B01F 11/0022 221/171 |
| 2005/0028617 A1 | * | 2/2005 | Wells | F16H 25/2025 73/864.91 |

FOREIGN PATENT DOCUMENTS

GB    2200469 A  *  8/1988  ............. G01G 17/04

OTHER PUBLICATIONS

Boivin et al., "Assessment of soil compaction using soil shrinkage modelling: Experimental data and perspectives", Soil & Tillage Research, 2006, vol. 88, pp. 65-79.
Braudeau et al., "Modeling the soil system: Bridging the gap between pedology and soil-water physics", Global and Planetary Change, 2009, vol. 67, pp. 51-61.
Braudeau et al., "Hydrostructural characteristics of two African tropical soils", European Journal of Soil Science, 2005, vol. 56, pp. 375-388.

* cited by examiner

*Primary Examiner* — Francis Gray
(74) *Attorney, Agent, or Firm* — Young & Thompson

(57) ABSTRACT

Apparatus for physically analyzing soil includes a sample changer for receiving at least two soil-sample holders, and having an element for placing each sample holder and sample thereof in a measurement area, in turns, according to a cycle repeated over time, the apparatus including: elements for measuring the size of the samples; elements for measuring the potential of the samples containing water; and elements for measuring the weight of the samples, wherein all of the measuring elements are grouped together in the measurement area so as to be simultaneously used implemented for a given sample when the latter is placed in the measurement area. The shrinkage curve and water potential curve, obtained from the measurements, represent the change, over time, in the status of the water and structure of the soil sample during the drying thereof, and can be used to determine the hydrostructural characteristics of the soil.

14 Claims, 5 Drawing Sheets

DEVICE FOR MEASUREMENT COUPLED WITH WATER PARAMETERS OF SOIL

TECHNICAL FIELD OF THE INVENTION

The present invention relates to the field of determining the properties of a complex structured medium, and more specifically to the field of instruments for physically characterizing porous samples.

It relates to an apparatus for physically analyzing soil, or another natural organized medium, that makes it possible to carry out, at regular time intervals and simultaneously, at least two measurements on the same sample relating to the water status of this sample, i.e. the water potential and shrinkage. The curves obtained from these measurements are representative of the change over time in the hydrological and structural status of the soil as it dries out.

PRIOR ART

It has been shown that accurate and reliable physical characterization of soil requires establishing two curves characteristic of the soil's humidity, namely the water potential curve and the shrinkage curve (Braudeau and Mohtar, 2009, Global Planetary Change Journal, 67: 51-61). In effect, these two curves are the equations of the thermodynamic and hydrostructural balance state of the organized medium that is a soil. They can be used to determine the nature of the soil studied and to characterize its physical properties with regard to its agricultural use.

The shrinkage curve represents the apparent specific volume of the sample (V, expressed in $dm^3$ per kg of dry soil) as a function of the gravimetric water content (designated W and expressed in kg of water per kg of dry soil). The soil water potential curve represents the water potential of the soil (designated h and expressed in kPa) also as a function of the water content W.

Currently, the shrinkage curve is measured under satisfactory conditions using an appliance, called a retractometer with sample changer, which was developed by the hydrophysical laboratory of the Institut de Recherche pour le Développement (Bondy IRD). The retractometer is the only apparatus currently capable of measuring the shrinkage curve of the soil continuously, i.e. at regular intervals of time during the gradual, continuous drying out of the sample (E. Braudeau, J. M. Costantini, G. Bellier, H. Colleuille, 1999, Soil. Sci. Soc. Am. J., 63: 525-535.).

The water potential curve is established by measuring the suction force exerted by the soil, i.e. in practice, the water tension in a non-saturated soil sample. The only method of directly measuring this physical magnitude is measurement using a tensiometer, well known in soil science. This tensiometer comprises, linked to a low pressure sensor, a small-diameter tube filled with water and fitted with a porous cup at its free extremity. The cup, which is planted in the center of the sample, letting water but not air pass through, the system is set in potential equilibrium with the water of the sample. The pressure sensor (e.g. a common pressure gauge) measures the tension of the water in the tensiometer.

To obtain the shrinkage and water potential curves, each of these two measurements is repeated during the drying out of the sample, over a period of time during which the sample passes from the wet state to the dry state. However, at the present time they are performed independently of each other, i.e. with a separate appliance, on different samples and under different laboratory conditions (air temperature and humidity). The characteristics, deduced from the curves obtained, are deduced by making the assumption that they relate to the same soil sample and that the measurement conditions are identical. This presents a significant drawback, not only on the duration as to the protocol for obtaining these two measurements but above all to the validity of the results. In particular, the reference, which is the saturated state of the sample, must be strictly identical for both curves.

To remedy these drawbacks, one wishes to carry out the measurement of these two basic physical characteristics of the soil on a single sample representative of the matrix structure of the soil horizon from which it was collected. It is also known that hydration/dehydration cycles modify the soil's behavior. It is therefore necessary for these measurements to be carried out simultaneously during a single dehydration cycle. It is also desired that several samples can be characterized in parallel, in particular when one wishes to have these characteristics for a series of samples, e.g. belonging to different horizons of a single soil profile.

The present invention was developed in order to fulfill this requirement. Its aim is to provide an apparatus measuring simultaneously the magnitudes required to establish two curves characteristic of the hydrological state of the soil, 1) on the same soil sample, 2) during a complete drying cycle and 3) under the same standard air temperature and humidity conditions. To date no apparatus allows this double measurement to be carried out on several samples at a time.

OBJECT OF THE INVENTION

More specifically, the aim of the invention is an apparatus for physically analyzing soil with regard to its hydrological state, comprising a sample changer that can receive at least two soil sample holders, said sample changer being equipped with means for placing each sample holder and its sample in a measurement area in turns and according to a cycle repeated over time, the apparatus comprising:
  means of measuring dimensions of said samples,
  means of measuring the water potential of said samples,
  means of measuring the mass of said samples,
all said measurement means being grouped in said measurement area to be utilized at the same time on a given sample when it is placed in said measurement area.

To establish the water potential and shrinkage curves, the measurements are repeated throughout the gradual drying out of the samples, i.e. during periods of, for example, 2 to 5 days. It is therefore especially advantageous to carry out the measurements on a series of several samples. The apparatus is therefore designed so that each of the samples is placed in turn in an area equipped with measurement means, called the measurement area, where the measurements are carried out. This cyclical movement of the samples is mainly achieved by means of a sample changer, whose structure will be described in detail later. The changer brings a sample and places it in the measurement area where it stays for a few moments, during which time all the measurement means are utilized to determine, at time t, the dimensions of the sample, its hydrological potential and its mass. These measurements are repeated cyclically, on each passage in the measurement area and without interruption, until completely dried.

The apparatus thus comprises a sample changer designed to allow measurements to be made on at least two samples. Ideally, however, one wishes to carry out measurements on a larger number of samples.

Thus, the apparatus that is the subject of the present invention comprises a sample changer, whose function is to make the samples circulate and bring them in turn into the measurement area, which advantageously comprises a circular tray having at least two through holes, each able to receive, supported on its edge, a substantially cylindrical sample holder, said tray being mobile in rotation and in vertical translation, such that when the tray is lowered, one of the sample holders with its sample is placed in the measurement area. When the measurements have been carried out, the tray rises, thereby raising the sample holder, then it advances a step and places the next sample in the measurement area, and so on.

The through holes are conveniently circular, with a diameter slightly greater than that of the base of the sample holders. The sample holders are suspended, freely supported, on the edge provided by the through holes. To do this, the holders can be fitted with a peripheral flange resting on said edge. The holders can also have a tapered portion that is held in the hole.

It is emphasized here that, while it is convenient to work on cylindrical samples, placed on similarly shaped holders, the present invention can equally well be utilized for other shapes, which also form part thereof. It is for reasons of clarity and simplicity that the present description only presents the apparatus equipped with substantially cylindrical sample holders.

The set of measurement means is grouped in the measurement area, i.e. within reach of the sample. The means of measuring the mass of the samples may conveniently be a balance, on whose pan the holder and its sample will be placed. The other measurements will be carried out from this location.

The sample's dimensions can be collected by different methods known to the person skilled in the art (e.g. by using elongation sensors, proximity sensors, etc.). According to the invention, an optical measurement method having no contact with the sample, by which the sample's diameter and height are measured, is preferred. The volume is then calculated, its change over time corresponding to the shrinkage value. The optical system's emitter and receiver units are placed close to the sample, in the measurement area.

Lastly, the water tension can be measured by a tensiometer, of a model available on the market or in laboratories such as, for example, a mini-tensiometer with a 2 mm diameter porous cup. This tensiometer must be placed in the measurement area so that it can collect the value of the water tension at the same time as the other measurements are taken. According to the invention, it is placed inside the sample holder, under the sample itself.

Thus, according to a preferred embodiment of the invention, the apparatus comprises:
 a balance with a pan able to receive and weigh the sample holder and its sample,
 an optical system for measuring the height and diameter of said sample when it is placed on said weighing pan, and
 for each sample, a tensiometer known as a "porous cup tensiometer" able to measure the water potential of said sample, comprising a flexible tube closed by a cup made of porous ceramic at one extremity and a pressure gauge at the other, said pressure gauge being housed in said sample's holder.

The principle of the porous cup tensiometer is well known in the field of soil sciences. The porous cup is sunk into the center of the sample. A capillary tube, generally made of flexible plastic, connects it to a pressure gauge. Pressure gauge designates the unit of the tensiometer that is sensitive to pressure variations in the fluid in a closed space. Different types of pressure gauge exist and can be utilized in the present invention. For example, a membrane pressure gauge placed in a chamber in contact with the capillary tube can be used. The deformation of the capillary tube is proportional to the pressure exerted in the chamber by the fluid. Measurement of the deformation, made for known pressures, makes it possible to obtain reference tables.

According to the invention, the pressure gauge is housed in said sample's holder. In other words, each sample holder hosts a pressure gauge whose porous cap is stuck in the sample it carries. Thus, when the holder is placed with its sample in the measurement area, the pressure reflecting the water potential of the sample can be collected, at the same time as the latter is weighed and its height and diameter are measured.

The tensiometer can be combined with the sample holder in various ways. According to an advantageous embodiment of the apparatus that is the subject of the present invention, each sample holder comprises:
 a substantially cylindrical base with a horizontal plate, designed to support a sample, mounted above it, and
 a pressure gauge unit fixed to the wall of said base, and wherein a hermetic chamber is formed communicating with said porous cap by means of said flexible tube, said chamber being associated with a membrane pressure sensor.

The horizontal plate can be fixed to the base by spacers, leaving a space between the plate and the base. This encourages the uniform evaporation of the water from the sample, particularly since perforations can advantageously be provided in said plate. The free space is turned to good account for passing the capillary tube from the chamber to the sample above.

The pressure gauge unit can be fixed to the wall of the base, preferably in its upper portion, by any means known to the person skilled in the art. In particular it can be screwed to the wall of the base, or be held by a shoulder provided on its rim cooperating with a complementary groove of the base, or otherwise.

It can comprise a recess forming a chamber, in which the pressure sensor is placed. According to a particular embodiment, the sensor can be attached to the bottom of the chamber, such that the chamber is closed by the sensor. In that case, an o-ring can advantageously ensure hermeticity. Thus, according to a preferred characteristic of the invention, each sensor forms a plug sealing the chamber.

According to another preferred characteristic of the invention, each chamber comprises a curved ceiling from the top of which a filler line fitted with a valve emerges. Before starting up the apparatus, the samples are placed on the horizontal plate, the porous cup tensiometers, previously filled with degassed water, are sunk from the side through to the center of the samples then connected to the pressure gauge units, also previously filled with water using the filler line ending in a valve. This operation must make it possible to obtain a system that only contains degassed water. Thanks to the geometry of the chamber and its inlet pipe, the formation of air bubbles during the filling of the chamber is prevented.

When a sample holder is placed on the pan of the balance, the measurements can begin. In particular, the values perceived by the pressure gauge must be transmitted to the operator or recorded for subsequent processing. It is not necessary for these values to be read continuously, it is sufficient for them to be collected at the same time as the other measurements (mass and dimensions).

This is why, in a particular embodiment of the apparatus according to the invention, each pressure gauge is connected to electrical contactors held close to the bottom of the base, and the pan of the balance is fitted with a board equipped with electrical terminals, the contactors being arranged so as to come into contact with the terminals when the sample holder is placed on the balance. A rod can be placed in the base to hold the contactors in the suitable position.

The measurements are carried out over several hours, even several days, during which the samples dry out gradually, the water evaporating and freeing up the porosity to be replaced by the atmospheric air. It is critical that the water-air exchanges are the most uniform possible throughout the thickness of the sample and on all sides. It has been seen that the horizontal plate can be fixed to the base by spacers, leaving a space between the plate and the base. The exchanges at the plate are further improved by perforations, large in number but small in size, so that the sample does not become destructured due to evaporation that may not be uniform all around the sample.

This is why the plate of each sample holder is preferably fitted with perforations permitting the water and air to pass between the atmosphere and the bottom of the sample.

As indicated earlier, the size of the sample placed in the measurement area is measured using an optical system. Conveniently, one has recourse to measurement by two sub-systems, one dedicated to measuring the diameter of the sample (insofar as it is cylindrical), the other dedicated to measuring its height. In a particular aspect according to the invention, the optical system for measuring the diameter of said sample comprises two laser barrier sensors placed in the measurement area either side of the sample when it is on the balance, at a mutual distance less than the assumed minimum diameter of the samples.

In general, the principle is that the measured object partially intercepts the laser beam. The size of the shadow, proportional to the object's diameter, corresponds to a certain amount of intercepted light. The reduction in the diameter is reflected by a change in the amount of light received (voltage). Two sensors of laser barrier photoelectric sensor type can be used. They allow the diameter of the soil sample to be determined at each passage throughout its drying-induced shrinkage. They will be placed at a distance relative to each other such that the sample cuts both beams together at the end of the process. To achieve this, they can be mounted on a horizontal rod such that their spacing can be adjusted conveniently at the start of the cycle. This rod also allows the distance between each sensor's emitter and receiver to be adjusted properly.

According to another aspect of the apparatus that is the subject of the invention, the optical system for measuring the height of said sample comprises a contactless laser sensor placed directly above the measurement area, able to emit a light beam towards a disk that is placed flat on the sample and to detect the reflected beam to determine by triangulation how far away said disk is. In general, this type of sensor calculates the distance that separates an object to be measured from a receiver (photodiode detector). In our case, the target will be a metal disk placed flat on the sample. This sensor therefore makes it possible to determine the variation in the height of the soil sample throughout its shrinkage. It can be mounted on a vertical rod such that its position can be adjusted conveniently at the start of the cycle.

According to a particularly advantageous characteristic of the present invention, the balance on which the holder and its sample are placed comprises a device for compensating the height according to the mass placed on its pan. It is understood that when water is replaced by air in the sample's porosity, the sample's mass changes, and as a result the pan of the balance is subjected to a smaller force in each cycle. The value measured by the sensor directly above the sample can thus be affected by this. It is possible to introduce a bias in the processing of the measurements carried out to take into account this loss of mass and the fact that the pan descends less and less far; for the invention, however, it was decided to utilize a means of keeping the pan fixed, regardless of the mass of the weighed object. Therefore, preferably a compensating balance is used, which allows measurements to be taken without moving the pan, accurate to a centigram.

It may be convenient to make sure that the sample holders are correctly oriented. According to an advantageous characteristic of the invention, the apparatus can comprise a positioning device, so that the holders and the samples are placed correctly, at the beginning and throughout the measurement. It can consist of a notch formed in the sample holders cooperating with a pointer formed on the edge of the holes of the circular tray. In this way the electrical terminals of the balance and the contactors of the pressure gauge will be made to coincide. The capillary tubes connecting the pressure gauge chamber to the porous cup will also be placed towards the center of the tray, away from the fields of the laser beams so as not disrupt with the optical measurement.

The units described above are assembled to operate together, and to determine the physical characteristics of several samples in a single operation. It goes without saying that, at least with regard to its duration, the process must be robotized and automated.

Thus, preferably, according to the invention, the sample changer comprises a circular tray comprising eight through holes, and a lifting column actioned by a first motor vertically moving the tray and by a second motor rotating said circular tray.

The apparatus according to the invention also comprises:
 a temperature-controlled oven able to contain at least the sample changer and all of the measurement means,
 means of controlling the sample changer and the measurement means,
 means of receiving and processing measured signals to obtain quantitative measurement data,
 means of recording the data elements, preferably as they are acquired.

The data elements are at least: the time, diameter, height, mass and low pressure in the tensiometer.

According to a particularly advantageous aspect of the invention, the apparatus comprises means of processing data recorded for each of the samples during a single evaporation cycle from the saturated state through to the dry state, and means of calculating the shrinkage curve and the water potential curve for said samples. The shrinkage curve V=f (W) and the potential curve h=f(W) are calculated. The curves can then be processed themselves with the help of predetermined models, with a view to characterizing the structure of the soil to which the sample belongs, or more generally the structure of the medium from which the sample was collected.

The present invention finds many applications, in particular for modeling BIO-SOIL-CLIMATE physical relationships in agro-environmental sciences, and also to establish a typology of soils (soil databases, soil maps) that can be used by soil ecology and biology laboratories.

The industrial sector working on developing new products in the agricultural and environmental guidance products now has a tool for testing and characterizing the behavior or the future of these products on the soil, taking into account the soil type under given climatic variability conditions. It is thus possible to predict the impact over the long term of these products which take into account the variety of soils and their hydrostructural and soil-climate operation.

The apparatus for the coupled measurement of two curves characteristic of the soil's humidity, the shrinkage curve and the water potential curve, is thus at the heart of a new methodology characterizing and modeling the hydrostructure of soils.

DESCRIPTION OF THE FIGURES

The present invention will be better understood, and details relating thereto will become apparent, thanks to the description that follows of one of its realization variants, with regard to the figures included in an appendix, wherein.

EXAMPLE 1

Coupled Measurement Apparatus

Figure 1:
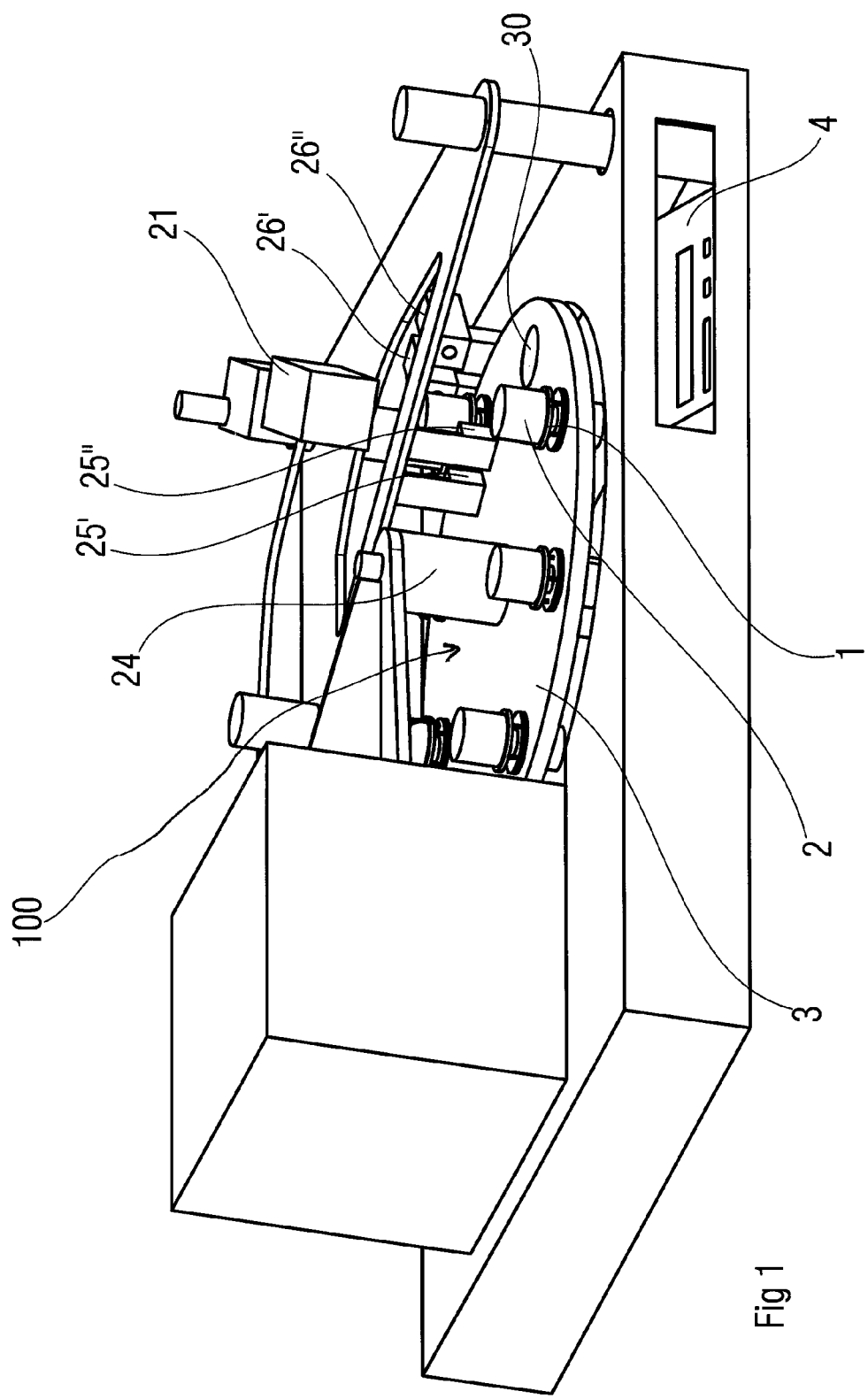
FIG. 1 is a perspective overview of the apparatus according to the invention.

FIG. 1 shows an apparatus for the quantitative determination of the physical characteristics of a soil according to the invention. It comprises the sample changer 100, which can receive eight sample holders 1. The changer 100 comprises the circular tray 3 in which there are eight through holes 30. It is associated to a lifting column 24 actioned by a motor vertically moving the circular tray 3. A second motor rotates the circular tray.

It also comprises means of measuring dimensions of said samples, means of measuring the water potential of said samples, and means of measuring the mass of said samples. These means are arranged so as to define a measurement area, in which samples 2 are placed to be subjected to said measurements.

The samples are typically cylindrical soil core samples, collected from a natural medium. They are saturated with water before being placed on the holders and subjected to the measurements.

The sample changer 100 is equipped with means for placing each sample holder 1 and its sample 2 in the measurement area in turns and according to a cycle repeated over time. It comprises the circular tray 3 equipped with at least eight through holes 30. Each hole 30 receives a sample holder 1, which rests supported on its edge. The through holes are circular, with a diameter slightly greater than that of the base 9 of the sample holders 1 (which will be described later).

Figure 2A:
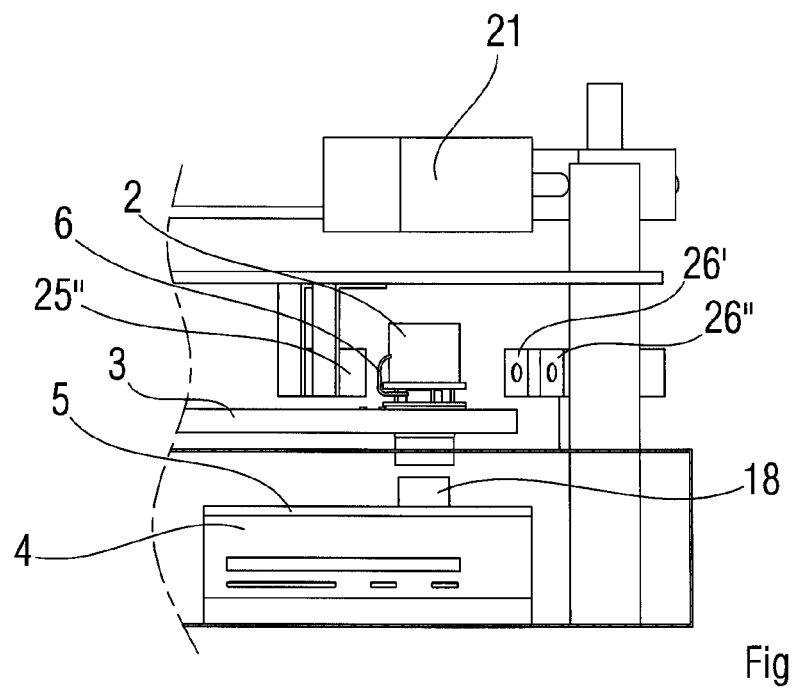
FIGS. 2a and 2b represent the measurement area of the apparatus according to the invention, before (2a) and after (2b) the sample is placed on the pan of the balance.
Figure 2B:
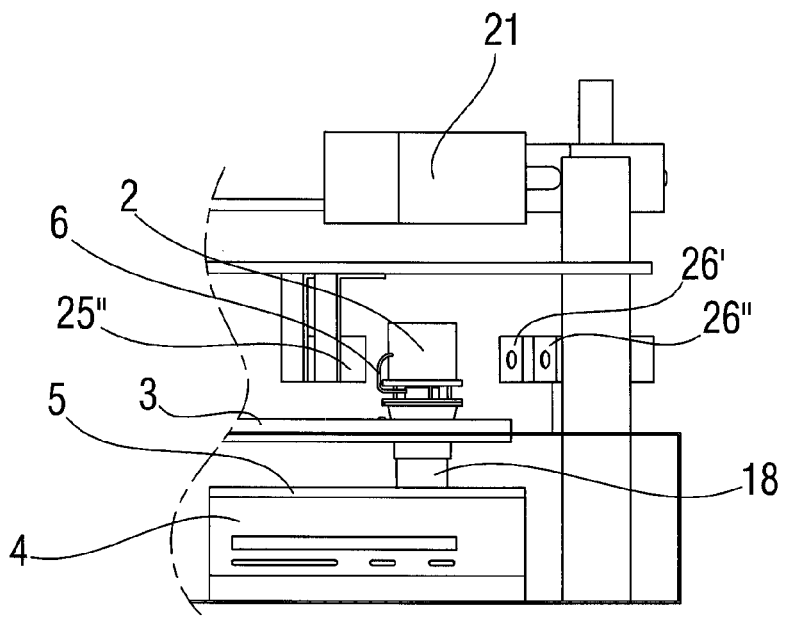
Figure 3:
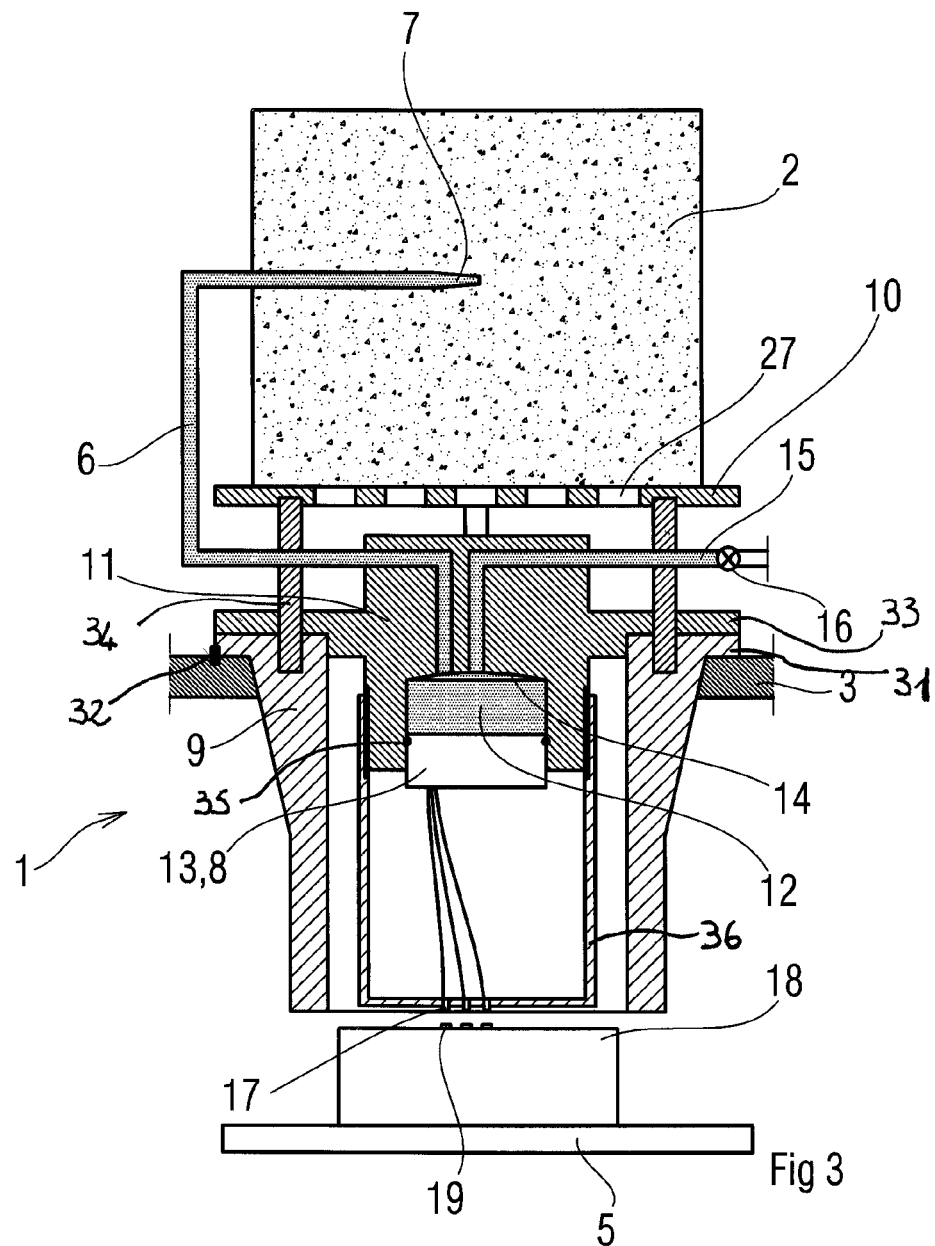
FIG. 3 is a cross-section view of a sample holder according to the invention, with its sample and its water tension measurement system.

The circular tray 3 is mobile in rotation and in vertical translation, such that when it is lowered, one of the sample holders 1 is placed with its sample 2 in the measurement area, as shown in FIGS. 2a and 2b. It is noted that the upper portion of the base 9 of the holders 1 comprises the flange 31, which rests on the edge of the hole 30 in the circular tray 3.

The means of measuring the mass of the samples 2 basically consists of a balance 4 (electronic balance accurate to a cg, 1,600 g capacity—model Mettler—Toledo PB 1502), on whose pan 5 a holder 1 and its sample 2 will be placed. Balance 4 is referred to as a "fixed platform balance", because it comprises a device for compensating the height of the pan according to the mass placed on it.

The pan of the balance is fitted with the board 18, which makes it possible to establish a temporary electrical connection between the sample holder placed above it and the units receiving and processing the data measured. To do this, the board 18 is equipped with electrical terminals 19, whose purpose is to establish the connection with contactors 17 borne by the sample holders. The terminals 19 will therefore be in contact successively and cyclically with the contactors 17 of the different sample holders as the measurements are taken.

The water tension is measured by a porous cup tensiometer. It comprises the capillary tube 6 made of flexible plastic, closed by the cup 7 made of permeable ceramic, which is sunk into the center of the sample. The other extremity of the flexible tube 6 is connected to the pressure gauge 8, which is housed in the sample holder 1, under the sample itself, such that it allows the value of the water tension to be collected at the same time as the other measurements are taken.

As illustrated in FIG. 2, associating the tensiometer and the sample holder is achieved by means of a support element, called the pressure gauge unit, incorporating the sensitive unit of the tensiometer, in this case a membrane pressure gauge. Each sample holder 1 comprises the base 9, with a cylindrical cross-section, with the horizontal plate 10, designed to support a sample, mounted on it. The horizontal plate 10 is pierced by perforations 27. It is fixed to the base 9 by spacers 34, leaving a space between the plate and the base.

The pressure gauge unit 11 fixed to the wall of the base 9, under the plate 10, by the shoulder 33 provided on its rim, which is mounted on the flange 31 of the base.

The pressure gauge unit 11 comprises a recess forming the hermetic chamber 12, in which the pressure sensor 13 is placed. The chamber 12 communicates with the porous cap 7 by means of the flexible tube 6. The sensor 13 is attached to the bottom of the chamber 12, such that the chamber is closed by the sensor. The o-ring 35 ensures the hermeticity of the assembly. The ceiling 14 of the chamber 12 is curved so that air bubbles are not trapped. The filler line 15, fitted with the valve 16, emerges from its top.

The sensor 13 is connected to the electrical contactors 17 held close to the bottom of the base 9. These contactors are arranged so as to come into contact with the electrical terminals 19 equipping the pan 5 of the balance 4, when the sample holder 1 is placed on it. The rod 36 is placed in the base to hold the contactors 17 in the suitable position.

When a sample holder 1 is placed on the pan 3 of the balance 4, the measurements begin. The values perceived by the pressure gauge 8 are transmitted to the operator or recorded for subsequent processing.

Lastly, the dimensions of the sample are taken by an optical method, through two sub-systems, one dedicated to measuring the diameter of the sample, the other dedicated to measuring its height.

Figure 4:
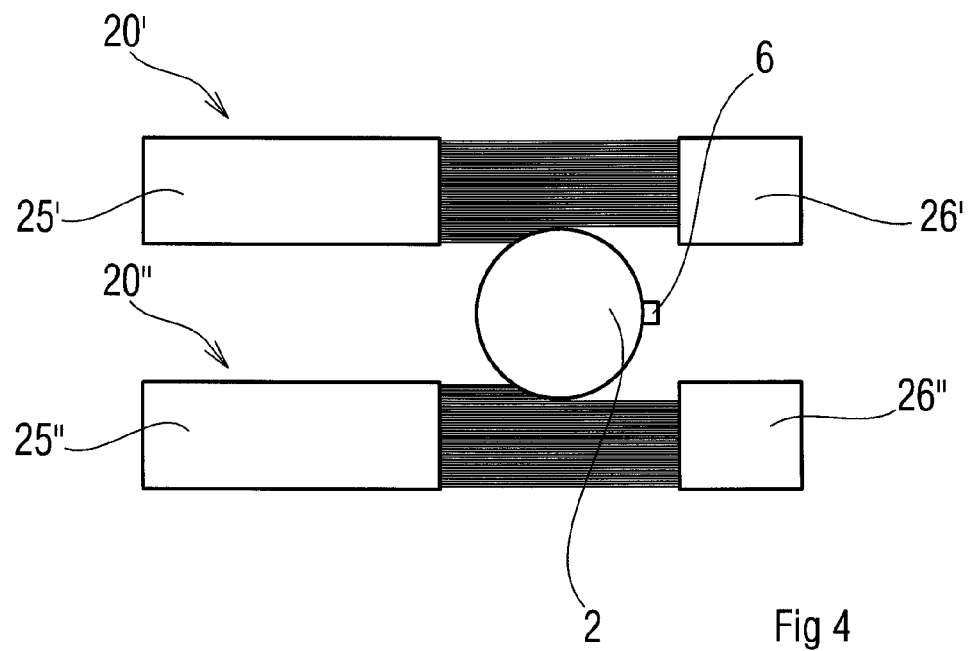
FIGS. 4 and 5 are schematic representations of the optical measurement systems.

As shown in FIG. 4, the optical system for measuring the diameter of the sample comprises two laser barrier sensors 20' and 20" (Keyence LX2-70 type laser barrier photoelectric sensors). The source 25' and 25" and the receiver 26' and 26" of each sensor are placed facing each other on either side of the measurement area, such that the sample cuts the beam when it is placed in the measurement area. The sensors 20' and 20" are mounted on horizontal rods (not shown) and the distance between them can be adjusted by sliding on the rod, such that it is less than the minimum diameter that the samples will have when they are completely dried out.

Figure 5:
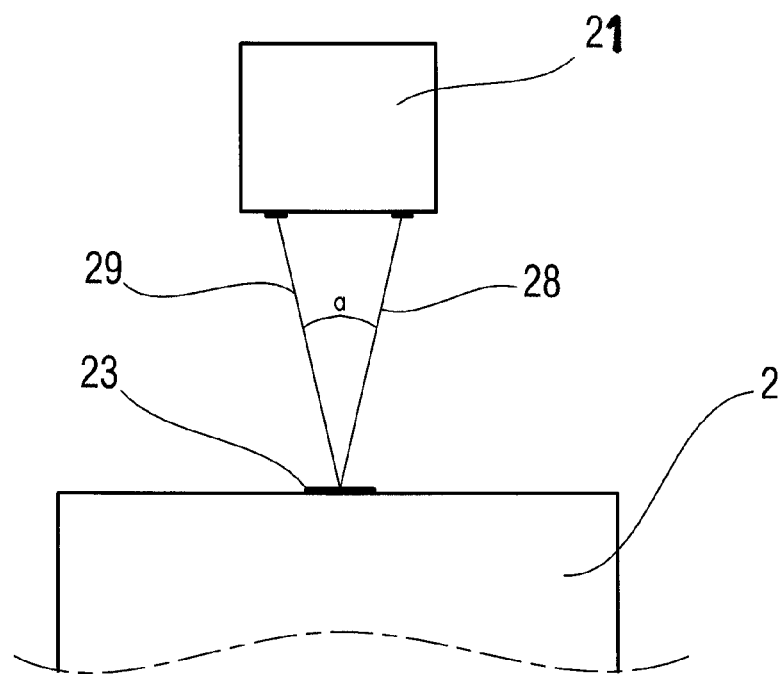

As shown in FIG. 5, the optical system for measuring the height of the sample 2 comprises the contactless laser sensor 21 (type Keyence LB72), placed directly above the measurement area. It emits a light beam 28 towards the metal disk 23 placed flat on the sample 2 and it detects the reflected beam 29. Then, the distance to the disk 23 is determined by the so-called triangulation method. The sensor 21 is mounted on a vertical rod (not shown) such that its position can be adjusted conveniently at the start of the cycle.

Thus, all said measurement means are grouped in the measurement area to be utilized at the same time on a given sample when it is placed in said measurement area. So that the holders 1 and samples 2 are placed correctly at the beginning and throughout the measurements, a notch is formed in the sample holders. It cooperates with a pointer 32 formed on the edge of each hole 30 of the circular tray 3.

The means and units that have just been described are arranged to form the apparatus according to the invention, which can comprise other elements commonly used for the correct operation of measurement equipment, such as a cover, height-adjustable feet, or others. It also comprises a temperature-controlled oven having a large enough volume to contain the sample changer and all of the measurement means.

The apparatus according to the example is associated to means of controlling the sample changer and the measurement means. It is assisted by means of receiving and processing signals to obtain quantitative measurement data, and means of recording data elements, preferably as they are acquired.

EXAMPLE 2

Implementation of the Apparatus on a Series of Eight Samples

Soil samples of approximately 100 cm3 collected from eight natural sites, to obtain eight cylinders with identical diameters, representative of the matrix structure of the soil horizon from which they were collected. The cylinders vary in size from 50 cm to 66 cm in diameter, and from 50 cm to 30 cm in height. The size is chosen appropriately according to the more or less clayey or sandy texture governing the stability of its structure, its uniformity, and the time that it will require to dry out.

After the saturation in water by infiltration per ascensum of the sample placed on a sheet of water for at least 4 hours, the eight samples are placed on each of the holders of the apparatus described in example 1. The porous cap is inserted into each sample and the chamber of the pressure gauge is filled with water. The holders thus equipped are placed in the holes of the sample changer, in the temperature-controlled oven at 30° C., such that the samples dry out regularly by evaporation of the water at a constant temperature, from the saturated state through to the dry state.

The apparatus is started. At regular intervals of approximately 10 minutes between each passage of the same sample, and for a duration of at least 2 days depending on the water capacity of the sample, it measures the following four variables for the series of eight samples: the diameter and height of the sample, its weight, and the water tension, measured using a tensiometer.

At each passage of a sample, the tray descends and positions the sample holder in front of the laser sensors, on the pan of the balance, on which a receptacle brings the power input/output terminals of the pressure sensor into contact with the apparatus control and data capture PLC.

The measurement data elements are recorded as the process progresses. The data elements collected are: the time, diameter, height, mass and low pressure in the tensiometer (from 0 to 80 kPa). These data elements are completed by several reference measurements taken at the end of the experiment (dry weight measurement of the samples brought to 105° C. in the oven, apparent dry volume measurement) so that the shrinkage curve, V=f(W), and potential curve, h=f(W), can be calculated.

Figure 6:
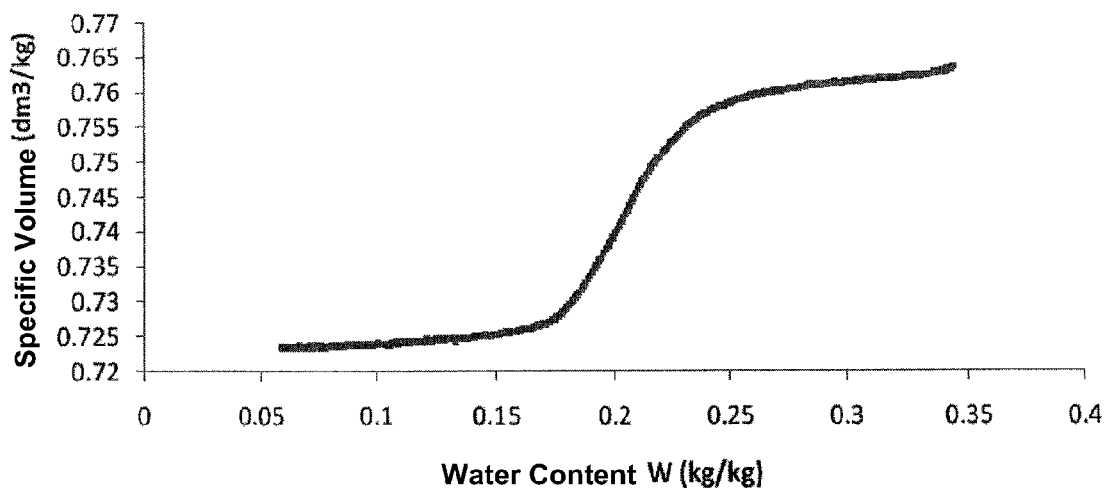
FIG. 6 is the shrinkage curve of one of the samples obtained using the apparatus according to the invention.
Figure 7:
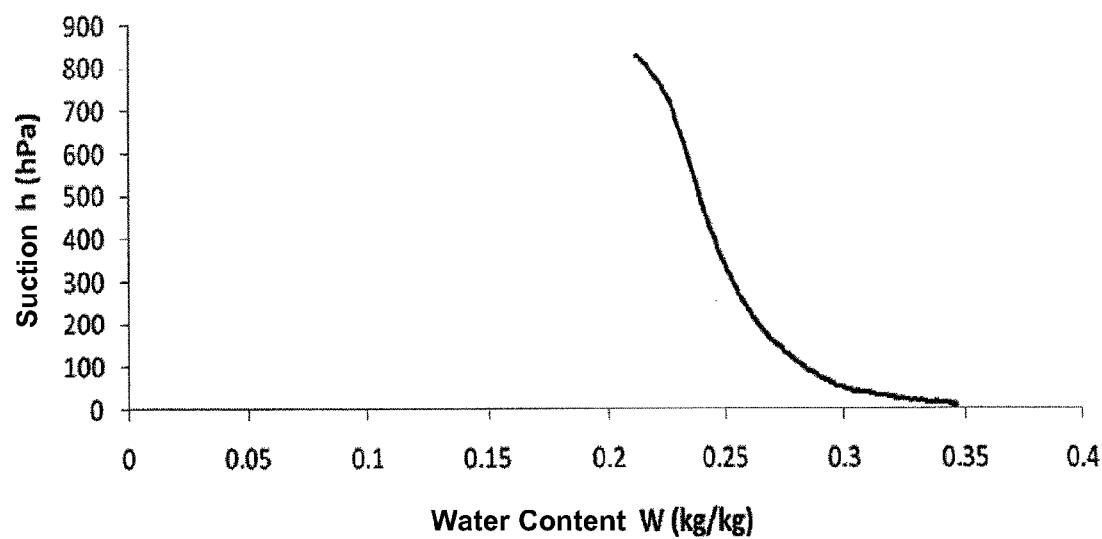
FIG. 7 is the water potential (or suction) curve of the same sample, obtained simultaneously using the apparatus according to the invention.

The shrinkage curve and water potential curve are plotted: see FIGS. 6 and 7. From these the specific volume V, water content W and the water potential h are deduced at time t between the wet state and the dry state.

The computerized processing of the two curves considered together will allow the hydrostructural parameters of the soil structure of the soils analyzed to be extracted.

The invention claimed is:

1. An apparatus for physically analyzing soil with regard to its hydrological state, comprising a sample changer (100) that can receive at least two soil sample holders (1), said sample changer being equipped with means for placing each sample holder and a sample (2) it holds in a measurement area in turns and according to a cycle repeated over time, wherein this apparatus comprises:
   means of measuring dimensions of said samples,
   means of measuring the water potential of said samples,
   means of measuring the mass of said samples,
   all said measurement means being grouped in said measurement area to be utilized at the same time on a given sample when it is placed in said measurement area.

2. The apparatus according to claim 1, wherein the sample changer comprises a circular tray (3) having at least two through holes (30), each able to receive, supported on its edge, a substantially cylindrical sample holder (1), said tray being mobile in rotation and in vertical translation, such that when the tray is lowered, one of the sample holders (1) with its sample (2) is placed in the measurement area.

3. The apparatus according to claim 1, wherein it comprises:
   a balance (4) with a pan (5) able to receive and weigh the sample holder (1) and its sample (2),
   an optical system for measuring the height and diameter of said sample when it is placed on said weighing pan, and
   for each sample, a tensiometer known as a "porous cup tensiometer" able to measure the water potential of said sample, comprising a flexible tube (6) closed by a cup (7) made of porous ceramic at one extremity and a pressure gauge (8) at the other, said pressure gauge being housed in said sample's holder.

4. The apparatus according to claim 3, wherein each sample holder (1) comprises:
   a substantially cylindrical base (9) with a horizontal plate (10), designed to support a sample (2), mounted above it, and
   a pressure gauge unit (11) fixed to the wall of said base, and wherein a hermetic chamber (12) is formed communicating with the porous cap (7) by means of the flexible tube (6), said chamber being associated with a membrane pressure sensor (13).

5. The apparatus according to claim 4, wherein each sensor (13) forms a plug sealing the chamber (12).

6. The apparatus according to claim 4, wherein each chamber (12) comprises a curved ceiling (14) from the top of which a filler line (15) fitted with a valve (16) emerges.

7. The apparatus according to claim 3, wherein each pressure gauge (8) is connected to electrical contactors (17) held close to the bottom of the base (9), and the pan (5) of the balance (4) is fitted with a board (18) equipped with electrical terminals (19), said contactors being arranged so as to come into contact with the terminals when the sample holder (1) is placed on the balance.

8. The apparatus according to claim 4, wherein the plate (10) of each sample holder (1) is fitted with perforations permitting the water and air to pass between the atmosphere and the bottom of the sample (2).

9. The apparatus according to claim 3, wherein the optical system for measuring the diameter of the sample (2) comprises two laser barrier sensors (20', 20") placed in the measurement area either side of said sample when it is placed on the balance (4), at a mutual distance less than the assumed minimum diameter of the samples.

10. The apparatus according to claim 3, wherein the optical system for measuring the height of the sample (2) comprises a contactless laser sensor (21) placed directly above the measurement area, able to emit a light beam towards a disk (23) that is placed flat on said sample and to detect the reflected beam to determine by triangulation how far away said disk is.

11. The apparatus according to claim 3, wherein the balance (4) comprises a device for compensating the height according to the mass placed on its pan (5).

12. The apparatus according to claim 1, wherein the sample changer (100) comprises a circular tray (3) comprising eight through holes (30), and a lifting column (24) actioned by a first motor vertically moving said circular tray and by a second motor rotating said circular tray.

13. The apparatus according to claim 1, wherein it comprises, in addition:
- a temperature-controlled oven able to contain at least the sample changer and all of the measurement means,
- means of controlling the sample changer and the measurement means,
- means of receiving and processing measured signals to obtain quantitative measurement data,
- means of recording the data elements.

14. The apparatus according to claim 1, wherein it comprises, in addition, means of processing data recorded for each of the samples during a single evaporation cycle from the saturated state through to the dry state, and means of calculating the shrinkage curve and the water potential curve for said samples.

\* \* \* \* \*